(12) United States Patent
Hyde et al.

(10) Patent No.: US 9,111,324 B2
(45) Date of Patent: Aug. 18, 2015

(54) PROGRAMMED DISPENSING OF CONSUMABLE COMPOSITIONS

(75) Inventors: Roderick A. Hyde, Redmond, WA (US);
Eric C. Leuthardt, St. Louis, MO (US);
Robert W. Lord, Seattle, WA (US);
Clarence T. Tegreene, Bellevue, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 620 days.

(21) Appl. No.: 12/074,245

(22) Filed: Feb. 29, 2008

(65) Prior Publication Data

US 2009/0144190 A1    Jun. 4, 2009

Related U.S. Application Data

(63) Continuation-in-part of application No. 11/998,461, filed on Nov. 29, 2007, now Pat. No. 8,788,380, and a continuation-in-part of application No. 12/001,061, filed on Dec. 7, 2007, now Pat. No. 8,718,817, and a continuation-in-part of application No. 12/001,063, filed on Dec. 7, 2007, now Pat. No. 7,804,419, and a continuation-in-part of application No. 12/002,794, filed on Dec. 18, 2007, now Pat. No. 8,457,783, and a continuation-in-part of application No. 12/004,094, filed on Dec. 19, 2007, now Pat. No. 8,362,914, and a continuation-in-part of application No. 12/006,252, filed on Dec. 31, 2007, now Pat. No. 8,758,677, and a continuation-in-part of application No. 12/012,500, filed on Feb. 1, 2008, now Pat. No. 7,919,042.

(51) Int. Cl.
*G06F 17/00* (2006.01)
*G08B 5/00* (2006.01)
*G06Q 50/22* (2012.01)
*G06Q 10/10* (2012.01)
*G06Q 40/02* (2012.01)

(52) U.S. Cl.
CPC ............... *G06Q 50/22* (2013.01); *G06Q 10/10* (2013.01); *G06Q 40/025* (2013.01)

(58) Field of Classification Search
CPC .......... A61K 2300/00; G06F 19/3456; G01N 2035/1062; G01N 21/80; A61B 5/0002
See application file for complete search history.

(56) References Cited

U.S. PATENT DOCUMENTS

| 4,223,801 | A | 9/1980 | Carlson |
| 4,310,103 | A | 1/1982 | Reilly, Jr. et al. |
| 4,641,692 | A | 2/1987 | Bennett |
| 4,823,982 | A | 4/1989 | Aten et al. |
| 4,899,839 | A | 2/1990 | Dessertine et al. |

(Continued)

OTHER PUBLICATIONS

U.S. Appl. No. 12/927,038, Hyde et al.

*Primary Examiner* — Mohammad Z Shaikh
(74) *Attorney, Agent, or Firm* — Suiter Swantz pc llo

(57) ABSTRACT

Methods and systems for programmed dispensation of consumable compositions are provided.
A method for administering a consumable composition may comprise: (a) dispensing a dose of a first consumable composition according to a programmed dosing schedule; and (b) detecting an identity of the first consumable composition.
A system for administering a consumable composition may comprise: (a) means for dispensing a dose of a first consumable composition according to a programmed dosing schedule; and (b) means for detecting an identity of the first consumable composition.

20 Claims, 11 Drawing Sheets

(56) References Cited

U.S. PATENT DOCUMENTS

| | | | | |
|---|---|---|---|---|
| 5,221,024 | A | 6/1993 | Campbell | |
| RE34,337 | E | 8/1993 | Bennett | |
| 5,329,459 | A | 7/1994 | Kaufman et al. | |
| 5,342,518 | A | 8/1994 | Posner et al. | |
| 5,372,276 | A | 12/1994 | Daneshvar | |
| 5,408,443 | A | 4/1995 | Weinberger | |
| 5,454,406 | A | 10/1995 | Rejret et al. | |
| 5,522,525 | A | 6/1996 | McLaughlin et al. | |
| 5,651,887 | A | 7/1997 | Posner et al. | |
| 5,681,507 | A | 10/1997 | Kazuma | |
| 5,752,621 | A | 5/1998 | Passamante | |
| 5,826,217 | A | 10/1998 | Lerner | |
| 5,850,344 | A * | 12/1998 | Conkright | 700/231 |
| 5,851,445 | A | 12/1998 | Kazuma | |
| 5,955,009 | A | 9/1999 | Kazuma | |
| 5,958,307 | A | 9/1999 | Kazuma | |
| 5,971,594 | A * | 10/1999 | Sahai et al. | 700/242 |
| 6,054,928 | A | 4/2000 | Lemelson et al. | |
| 6,068,156 | A | 5/2000 | Liff et al. | |
| 6,113,080 | A | 9/2000 | Kazuma | |
| 6,182,453 | B1 | 2/2001 | Forsberg | |
| 6,183,691 | B1 | 2/2001 | Swank et al. | |
| 6,249,717 | B1 | 6/2001 | Nicholson et al. | |
| 6,252,494 | B1 | 6/2001 | Howell | |
| 6,263,259 | B1 | 7/2001 | Bartur | |
| 6,304,797 | B1 | 10/2001 | Shusterman | |
| 6,330,957 | B1 | 12/2001 | Bell-Greenstreet | |
| 6,332,100 | B1 | 12/2001 | Sahai et al. | |
| 6,490,920 | B1 * | 12/2002 | Netzer | 73/304 C |
| 6,529,801 | B1 | 3/2003 | Rosenblum | |
| 6,539,281 | B2 | 3/2003 | Wan et al. | |
| 6,604,650 | B2 | 8/2003 | Sagar | |
| 6,625,518 | B2 | 9/2003 | Depeursinge | |
| 6,636,780 | B1 * | 10/2003 | Haitin et al. | 700/236 |
| 6,684,920 | B2 | 2/2004 | Seitz et al. | |
| 6,697,704 | B2 | 2/2004 | Rosenblum | |
| 6,732,884 | B2 | 5/2004 | Topliffe et al. | |
| 6,766,218 | B2 | 7/2004 | Rosenblum | |
| 6,773,668 | B1 | 8/2004 | Everson et al. | |
| 6,801,123 | B2 | 10/2004 | Brakus | |
| 6,856,932 | B1 | 2/2005 | Wallace | |
| 6,892,941 | B2 | 5/2005 | Rosenblum | |
| 7,072,738 | B2 * | 7/2006 | Bonney et al. | 700/237 |
| 7,175,081 | B2 | 2/2007 | Andreasson et al. | |
| 7,295,890 | B2 | 11/2007 | Jean-Pierre | |
| 7,440,818 | B2 | 10/2008 | Handfield et al. | |
| 7,444,203 | B2 | 10/2008 | Rosenblum | |
| 7,454,267 | B2 * | 11/2008 | Bonney et al. | 700/237 |
| 7,469,820 | B2 | 12/2008 | Rosenblum | |
| 7,471,993 | B2 | 12/2008 | Rosenblum | |
| 7,502,664 | B2 | 3/2009 | Berg | |
| 7,516,082 | B2 | 4/2009 | Sanville et al. | |
| 7,616,111 | B2 * | 11/2009 | Covannon et al. | 340/539.12 |
| 7,630,791 | B2 | 12/2009 | Nguyen et al. | |
| 7,715,277 | B2 * | 5/2010 | de la Huerga | 368/10 |
| 7,774,097 | B2 | 8/2010 | Rosenblum | |
| 7,804,419 | B2 * | 9/2010 | Hyde et al. | 340/815.4 |
| 7,831,336 | B2 | 11/2010 | Gumpert | |
| 7,844,361 | B2 | 11/2010 | Jean-Pierre | |
| 7,907,477 | B2 * | 3/2011 | Puzia | 368/10 |
| 7,919,042 | B2 * | 4/2011 | Hyde et al. | 422/24 |
| 7,925,890 | B2 * | 4/2011 | Dever et al. | 713/189 |
| 8,019,471 | B2 | 9/2011 | Bogash et al. | |
| 8,060,249 | B2 | 11/2011 | Bear et al. | |
| 8,068,015 | B2 | 11/2011 | Burg | |
| 8,116,907 | B2 * | 2/2012 | Hyde et al. | 700/236 |
| 8,195,330 | B2 | 6/2012 | Coe | |
| 8,325,011 | B2 | 12/2012 | Butler et al. | |
| 8,362,914 | B2 * | 1/2013 | Hyde et al. | 340/815.4 |
| 8,457,783 | B2 * | 6/2013 | Hyde et al. | 700/240 |
| 8,652,412 | B2 * | 2/2014 | Hyde et al. | 422/292 |
| 8,718,817 | B2 * | 5/2014 | Hyde et al. | 700/231 |
| 8,718,819 | B2 * | 5/2014 | Hyde et al. | 700/240 |
| 8,758,677 | B2 * | 6/2014 | Hyde et al. | 422/1 |
| 8,788,380 | B2 * | 7/2014 | Hyde et al. | 705/35 |
| 2001/0011501 | A1 | 8/2001 | Sato et al. | |
| 2001/0045242 | A1 | 11/2001 | Clusserath et al. | |
| 2002/0001535 | A1 | 1/2002 | Weng | |
| 2002/0088817 | A1 | 7/2002 | Bell-Greenstreet | |
| 2003/0050731 | A1 | 3/2003 | Rosenblum | |
| 2003/0084957 | A1 | 5/2003 | Seitz et al. | |
| 2003/0088332 | A1 | 5/2003 | Rosenblum | |
| 2003/0093181 | A1 | 5/2003 | Rosenblum | |
| 2003/0140921 | A1 * | 7/2003 | Smith et al. | 128/200.14 |
| 2003/0220608 | A1 * | 11/2003 | Huitt et al. | 604/29 |
| 2004/0078218 | A1 * | 4/2004 | Badinelli | 705/2 |
| 2004/0163970 | A1 * | 8/2004 | Sin et al. | 205/792 |
| 2004/0164146 | A1 | 8/2004 | Rosenblum | |
| 2004/0215369 | A1 | 10/2004 | Rosenblum | |
| 2004/0249250 | A1 | 12/2004 | McGee et al. | |
| 2005/0065645 | A1 | 3/2005 | Liff et al. | |
| 2006/0097000 | A1 | 5/2006 | Gumpert | |
| 2006/0189552 | A1 * | 8/2006 | Vishnupad et al. | 514/29 |
| 2006/0218011 | A1 | 9/2006 | Walker et al. | |
| 2006/0259195 | A1 | 11/2006 | Eliuk et al. | |
| 2006/0266763 | A1 | 11/2006 | Svabo Bech | |
| 2006/0283876 | A1 | 12/2006 | Mocnik et al. | |
| 2007/0145067 | A1 | 6/2007 | Headlee | |
| 2007/0184219 | A1 | 8/2007 | Johnson | |
| 2007/0186923 | A1 * | 8/2007 | Poutiatine et al. | 128/200.14 |
| 2007/0212411 | A1 * | 9/2007 | Fawzy et al. | 424/457 |
| 2007/0293982 | A1 | 12/2007 | Rosenblum | |
| 2008/0173705 | A1 | 7/2008 | Girard et al. | |
| 2008/0195251 | A1 | 8/2008 | Milner | |
| 2008/0283542 | A1 | 11/2008 | Lanka et al. | |
| 2009/0048712 | A1 | 2/2009 | Rosenblum | |
| 2009/0057341 | A1 | 3/2009 | Girard et al. | |
| 2009/0134181 | A1 | 5/2009 | Wachman et al. | |
| 2009/0144189 | A1 * | 6/2009 | Leuthhardt et al. | 705/38 |
| 2010/0261286 | A1 * | 10/2010 | Kim et al. | 436/149 |
| 2010/0324728 | A1 | 12/2010 | Rosenblum | |

\* cited by examiner

PROGRAMMED DISPENSING OF CONSUMABLE COMPOSITIONS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/998,461, entitled Programmed Dispensing of Consumable Compositions, naming Eric C. Leuthardt, Clarence T. Tegreene, Lowell L. Wood, Jr., Roderick A. Hyde and Robert W. Lord as inventors, filed Nov. 29, 2007 now U.S. Pat. No. 8,788,380, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,061, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007, now U.S. Pat. No. 8,718,817 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/001,063, entitled Programmed Dispensing of Consumable Compositions, naming Roderick A. Hyde, Eric C. Leuthardt, Robert W. Lord, Clarence T. Tegreene, and Lowell L. Wood, Jr. as inventors, filed Dec. 7, 2007, now U.S. Pat. No. 7,804,419 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/002,794, entitled Communications Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 18, 2007, now U.S. Pat. No. 8,457,783 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/004,094, entitled Communications Regarding Aspects of a Consumable Composition, naming Roderick A. Hyde, Eric C. Leuthardt, Robert W. Lord, Clarence T. Tegreene, and Lowell L. Wood, Jr. as inventors, filed Dec. 19, 2007, now U.S. Pat. No. 8,362,914 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,252, entitled Sterilization of Consumable Composition Dispensers, naming Roderick A. Hyde, Eric C. Leuthardt, Robert W. Lord, Clarence T. Tegreene, and Lowell L. Wood, Jr. as inventors, filed Dec. 31, 2007, now U.S. Pat. No. 8,758,677 which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/012,500 entitled Sterilization of Consumable Composition Dispensers, naming Roderick A. Hyde, Eric C. Leuthardt, Robert W. Lord, Clarence T. Tegreene, and Lowell L. Wood, Jr. as inventors, filed Feb. 1, 2008, now U.S. Pat. No. 7,919,042 which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, *Benefit of Prior-Filed Application*, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

Programmed regimens of consumable compositions may be prescribed by a physician or may simply be desirable for the health and well-being of an individual. However, confusion may arise concerning the schedule, dosage, and/or compliance with a programmed dosing regimen.

DETAILED DESCRIPTION

Figure 1:
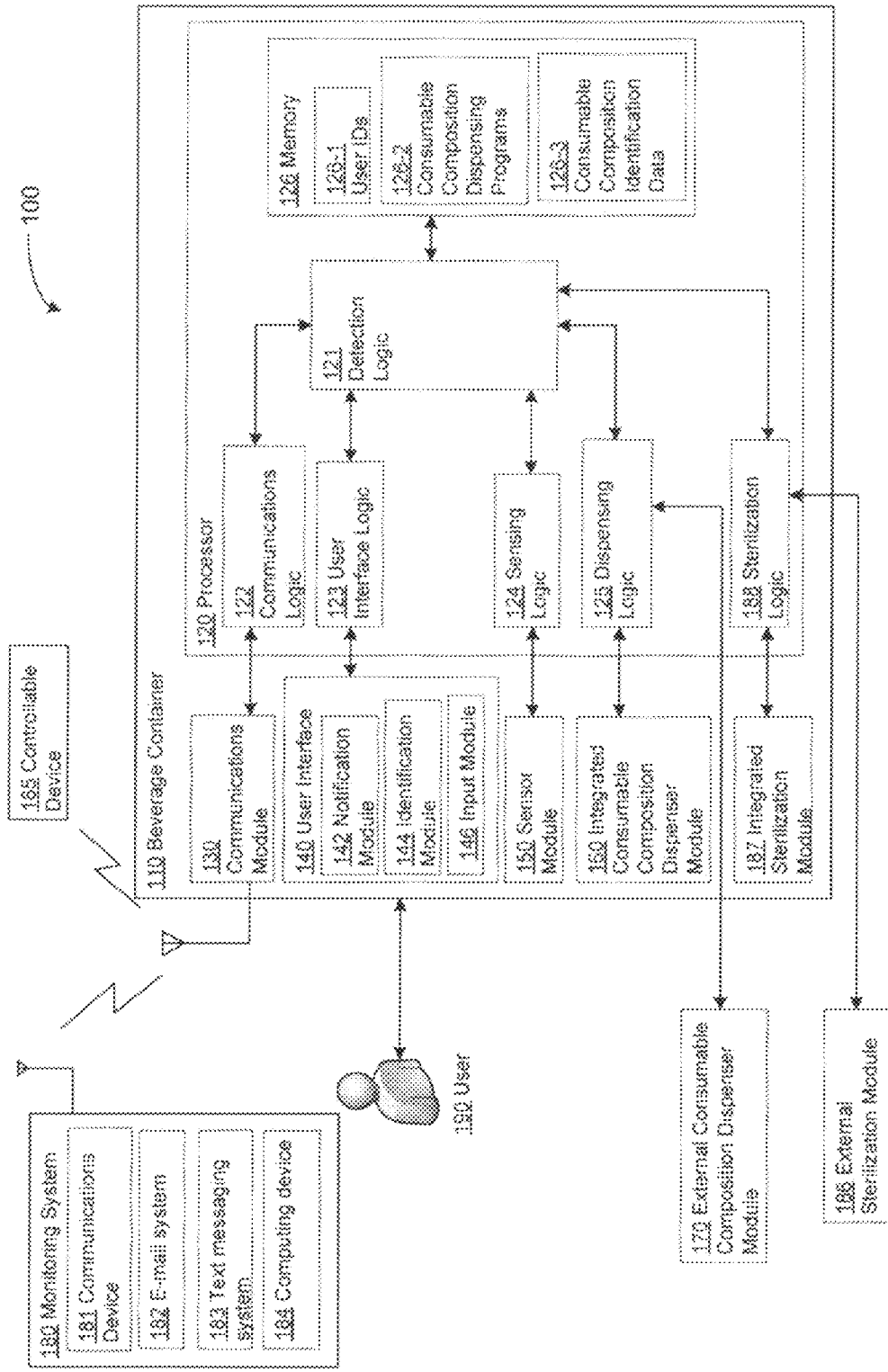
FIG. 1 shows a high-level block diagram of a beverage container.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates an example environment in which one or more technologies may be implemented. A consumable composition dispensing system 100 may comprise a beverage container 110 to be used by user 190. The beverage container 110 may be any receptacle configured for retaining a liquid or gel composition. For example, the beverage container 110 may include a cup, glass, mug, bowl, pitcher, jug, or the like.

The beverage container 110 may include a processor 120 (e.g. a microprocessor), a communications module 130 (e.g. a cellular transceiver, a Bluetooth transceiver, a WiFi transceiver, a satellite transceiver), a user interface 140 (e.g. display, touchscreen, keypad, speaker system), a sensor module 150 (e.g. a thermometer, barometer, concentration sensor, biometric sensor, accelerometer, UV sensor) an integrated consumable composition dispenser module 160 (e.g. injector, mechanical dispenser) and/or an integrated sterilization module 187 (e.g. a heating element).

The integrated consumable composition dispenser module 160 may be physically incorporated as a component of the beverage container 110. The integrated consumable composition dispenser module 160 may include an actuated mechanical apparatus which opens in response to a command from dispensing logic 125, thereby dispensing a dose of the consumable composition. The beverage container 110 may be configured to receive a dose of the consumable composition via gravitational flow or by pressurized injection of the dispensed composition from the integrated consumable composition dispenser module 160.

The external consumable composition dispenser module 170 may be physically separated from the beverage container 110. The external consumable composition dispenser module 170 may include a mechanical apparatus which opens in response to a command from dispensing logic 125 so as to introduce a dose of the consumable composition into the beverage container 110. The beverage container 110 may be configured to receive a dose of the consumable composition via a communicating assembly whereby the beverage container 110 may be physically coupled to the external consumable composition dispenser module 170 via a mutual conduit operably configured to allow the passage of the consumable composition between the external consumable composition dispenser module 170 and the beverage container 110.

Processor 120 may include communications logic 122, user interface logic 123, sensing logic 124, dispensing logic 125, memory 126, and/or sterilization logic 188.

Memory 126 may include user IDs 126-1 (e.g. user fingerprint data), consumable composition dispensing programs 126-2 (e.g. scheduled dosing regimens), and/or consumable composition identification data 126-3 (e.g. spectroscopic data for various consumable compositions).

User interface 140 may include a notification module 142 (e.g. an LED), an identification module 144 (a fingerprint scanner), and/or an input module 146 (a microphone).

Sensor module 150 may include one or more of a light source sensor, a position sensor, an emission sensor, a spectrophotometer, an infrared or ultraviolet sensor, a biometric sensor or the like. Sensor module 150 may include a biometric sensor which senses the presence of saliva, perspiration, sebum or the like, either on the surface of the beverage container 110 or as a component of the contents therein. Sensor module 150 may include an accelerometer, an inertial motion sensor, or the like, which may sense the movement of the beverage container 110. Sensor module 150 may include a fiber optic pressure sensor, mechanical deflection pressure sensor, strain gauge pressure sensor, piezoresistive pressure sensor, microelectromechanical (MEMS) pressure sensor, variable capacitance pressure sensor, or the like which senses a pressure applied to the beverage container 110. Sensor module 150 may include a capacitive concentration sensor which may sense a concentration of the consumable composition present in the beverage container 110. Sensor module 150 may include an inclinometer or the like. Sensor module 150 may include a flowmeter for sensing a flowrate into or out of the beverage container 110. Sensor module 150 may include a capacitive level sensor, such as a strip or dual-probe sensor (e.g., a strip running down that side of the cup to sense a fluid level based at least in part between differences in the known/inferred/assumed dielectric constants of air and a fluid). In some instances, the dielectric constant is recalled/calculated in response to a sensed composition of a fluid (e.g., sensed constituents of an alcoholic cocktail); in other instances, the dielectric constant is assumed (e.g., defaults to that of water). Sensor module 150 may include an electrochemical analyzer (e.g. an electrode pair disposed within an electrolyte capable of measuring an electrochemical reaction) for measuring a concentration of a gas in an atmosphere. Sensor module 150 may include a chemical composition analysis mechanism (e.g. photoionization sensors, spectroscopic sensors, spectrometric sensors, crystallographic sensors, electrochemical sensors, calorimetric sensors).

The consumable composition dispensing system 100 may further include an external consumable composition dispenser module 170 (e.g. injector, mechanical dispenser) and/or external sterilization module 186 (e.g. an autoclave).

Monitoring system 180 may relay a notification (e.g. a notification that a chemical interaction between two or more consumable compositions may occur) received from communications module 130 to a communications device 181 (e.g. a cell phone, satellite phone, Blackberry®, and/or land-line phone), e-mail system 182 (e.g. an IMAP, POP3, SMTP, and/or HTTP e-mail server having an e-mail account associated with a user 190), text messaging system 183 (e.g. SMS system in GSM) and/or a computing device 184 (e.g. a personal digital assistant (PDA), personal computer, laptop, music player and/or gaming device).

The consumable composition may be a pharmaceutical composition including, but not limited to, one or more of the following: 5-alpha reductase inhibitors, 5-HT antagonists, ACE inhibitors, adrenergic agonists, adrenergic neurone blockers, alkalising agent, alpha blockers, aminoglycosides, anaesthetics, analgesics, androgens, angiotensin receptor blockers, anti-allergics, antiandrogens, antianginals, antiarrhythmics, antibiotics, anticholinergics, anticholinesterase, anticoagulants, anticonvulsants, antidepressants, antidiarrhoeals, antidopaminergics, anti-emetics, antiepileptics, antiflatulents, antifungal, antifungals, anti-hemophilics, antihistamine, antihistamines, antiplatelets, antipsychotics, antiseptics, antispasmodic, antispasmodics, antithyroid drugs, antitussives, anxiolytics, astringents, barbiturates, benzodiazepine, beta-receptor antagonists, beta-receptor blocker, bile acid sequestrants, bronchodilators, calcitonins, calcium channel blockers, cannabinoids, carbonic anhydrase inhibitors/hyperosmotics, cardiac glycosides, cerumenolyti, cholinergics, corticosteroids, COX-2 selective inhibitors, cycloplegics, cyclopyrrolone, cytoprotectants, decongestants, diphosphonates, diuretics, dopamine antagonist, emetic, fibrinolytics, fluoroquinolones, gonadotropins, growth hormones, H2-receptor antagonists, haemostatic drugs, heparins, hormonal contraceptives, hypnotics, hypolipidaemic agents, imidazoles, immunoglobulins, immunosuppressants, insulin, interferons, laxatives, local anesthetics, mast cell inhibitors, miotics, monoclonal antibodies, movement disorder drugs, mucolytics, muscle relaxants, mydriatics, neuromuscular drugs, nitrates, nitroglycerin, NSAIDs, ocular lubricants, opioids, parasympatholytics, parasympathomimetics, peripheral activators, polyenes, prostaglandin agonists/prostaglandin inhibitors, prostaglandin analogues, proton pump inhibitors, quinolones, reflux suppressants, selective alpha-1 blocker, sildenafil, statins, steroids, stimulants, sulfa drugs, sympathomimetics, thyroid hormones, topical anesthetics, topical antibiotics, vaccines, vasoconstrictors, vasodilators, vasopressin analogues, or the like.

The consumable composition may be a neutraceutical composition including, but not limited to, one or more of the following: vitamins (e.g., ascorbic acid, pyridoxine, riboflavin), minerals (e.g., calcium salts, zinc salts, potassium salts), hormones (e.g., dimethylaminoethanol (DMAE), dehydroepiandrosterone (DHEA), melatonin), biochemicals (e.g., adenosine triphosphate, coenzyme A, cysteine), glandulars (e.g., edible compositions derived from glandular organs of animals such as the thyroid, pancreas, adrenal cortex), herbals (e.g., ginkgo, garlic, goldenseal, echinacea), or the like.

Figure 2:
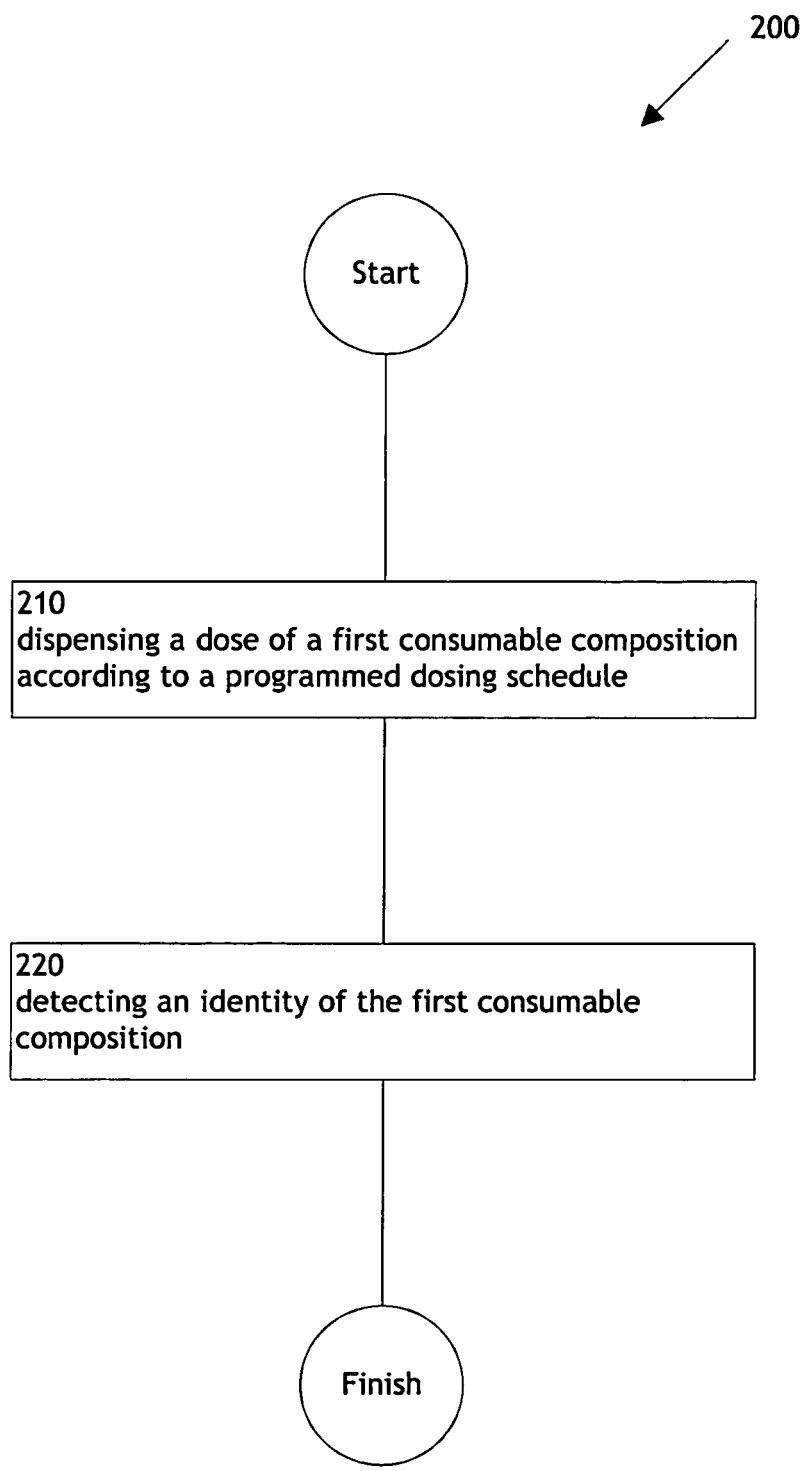
FIG. 2 is a high-level logic flowchart of a process.

FIG. 2 illustrates an operational flow 200 representing example operations related to detecting interactions between dispensed consumable compositions. In FIG. 2 and in following figures that include various examples of operational flows, discussion and explanation may be provided with respect to the above-described examples of FIG. 1, and/or with respect to other examples and contexts. However, it should be understood that the operational flows may be executed in a number of other environments and contexts, and/or in modified versions of FIG. 1. Also, although the various operational flows are presented in the sequence(s) illustrated, it should be understood that the various operations may be performed in other orders than those which are illustrated, or may be performed concurrently.

After a start operation, the operational flow 200 moves to an operation 210. Operation 210 depicts dispensing a dose of a first consumable composition according to a programmed dosing schedule (e.g. distributing a pharmaceutical composition in accordance with a user or physician-defined regimen). For example, as shown in FIG. 1, an integrated consumable composition dispenser module 160, and/or an external consumable composition dispenser module 170 may distribute one or more doses (e.g. 30 mg) of a consumable composition (e.g., an anti-depressant, such as Paroxotene) into a beverage container 110 (e.g., a drinking cup) according to a programmed dosing schedule (e.g. electronic data representing a physician-prescribed regimen of medication maintained in memory 126).

Then, operation 220 depicts detecting an identity of the first consumable composition (e.g. spectroscopic measurement of the composition of a biochemical). For example, as shown in FIG. 1, sensing logic 124 may cause sensor module 150 to detect an identity (e.g. a chemical composition) of a consumable composition. Sensor module 150 may include a chemical composition analysis mechanism (e.g. photoionization sensors, spectroscopic sensors, spectrometric sensors, crystallographic sensors, electrochemical sensors, calorimetric sensors). Identity data regarding the first consumable composition may be compared to consumable composition identification data 126-3 maintained in memory 126 so as to determine an identity of the first consumable composition.

Figure 3:
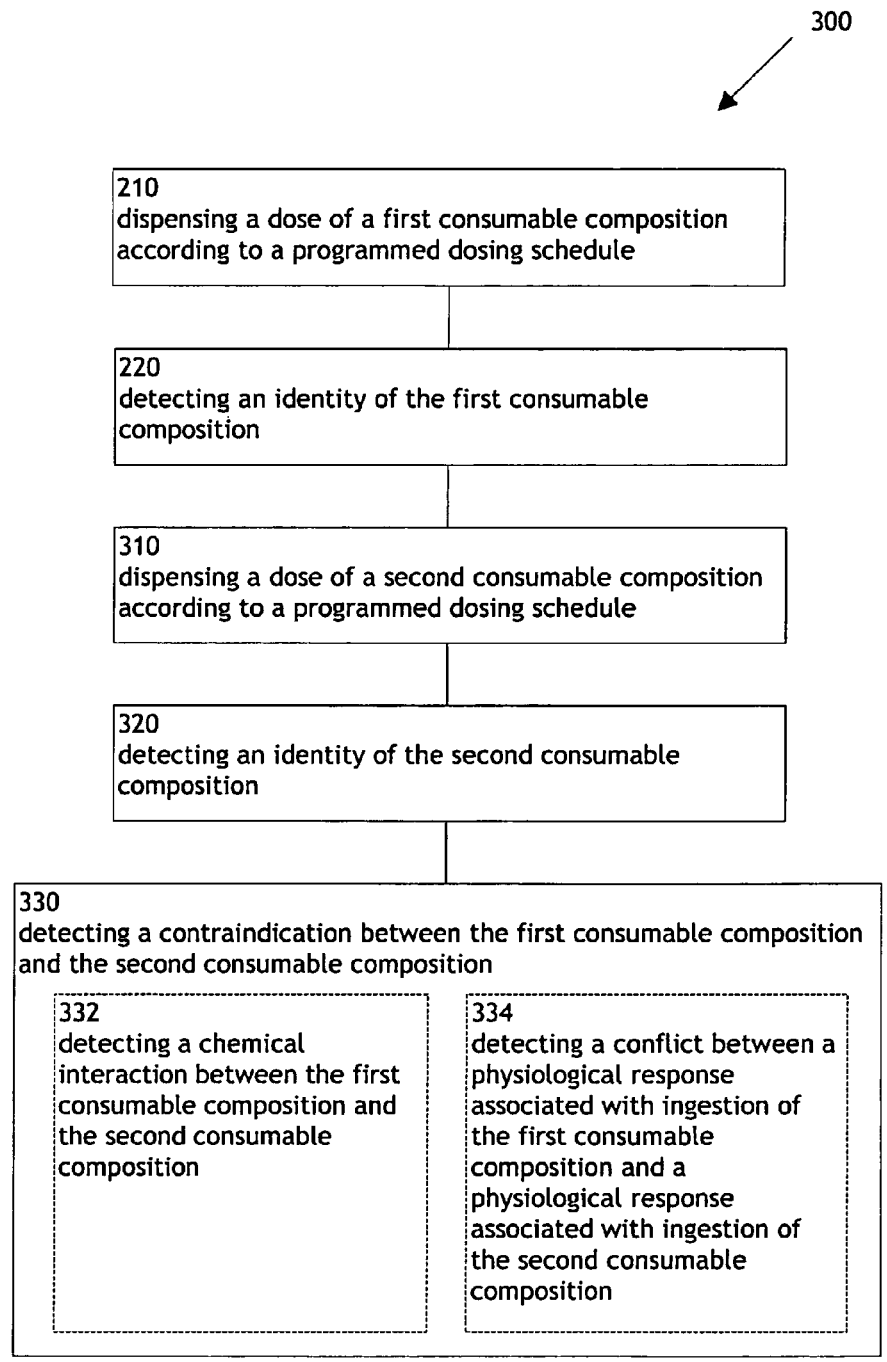
FIG. 3 is a high-level logic flowchart of a process.

FIG. 3 illustrates an operational flow 300 representing example operations related to retrospective detection of interactions between dispensed consumable compositions. FIG. 3 illustrates an example embodiment where the example operational flow 200 of FIG. 2 may include at least one additional operation. Additional operations may include an operation 310, an operation 320, an operation 330, an operation 332 and/or an operation 334.

After a start operation, an operation 210, and an operation 220, the operational flow 300 moves to an operation 310. Operation 310 illustrates dispensing a dose of a second consumable composition according to a programmed dosing schedule (e.g. distributing a neutraceutal composition in accordance with a homeopathic regimen). For example, as shown in FIG. 1, an integrated consumable composition dispenser module 160, and/or an external consumable composition dispenser module 170 may distribute one or more doses (e.g. 20 mg) of a consumable composition (e.g., a vitamin B-12 supplement) into a beverage container 110 according to a programmed dosing schedule (e.g. electronic data representing a user-defined regimen of a neutraceutical maintained in memory 126).

Then, operation 320 illustrates detecting an identity of the second consumable composition (e.g. spectrometric measurement of the composition of a mineral). For example, as shown in FIG. 1, sensing logic 124 may cause sensor module 150 to detect an identity (e.g. a chemical composition) of a consumable composition. Identity data regarding the second consumable composition may be compared to consumable composition identification data 126-3 maintained in memory 126 so as to determine an identity of the second consumable composition.

Then, operation 330 illustrates detecting a contraindication between the first consumable composition and the second consumable composition (e.g. detecting a combination of consumable compositions which, when ingested within a proximate time period, may be harmful to a user). For example, as shown in FIG. 1, the identity of the first consumable composition and the second consumable composition may be compared to consumable composition identification data 126-3 for consumable compositions which may be generally contraindicated for one another or specifically contraindicated for a particular user 190.

The operation 332 illustrates detecting a chemical interaction between the first consumable composition and the second consumable composition (e.g. detecting a deactivation of the functionality of a pharmaceutical consumable composition by a vitamin supplement). For example, as shown in FIG. 1, the identity of the first consumable composition and the second consumable composition may be compared to consumable composition identification data 126-3 for consumable compositions which may be chemically incompatible (e.g. the first and second consumable compositions react chemically to produce a third undesirable composition).

The operation 334 illustrates detecting a conflict between a physiological response associated with an ingestion of the first consumable composition and a physiological response associated with an ingestion of the second consumable composition (e.g. detecting proximate dispensations of an anticoagulant, such as warfarin, and a blood pressure medication, such as a beta-blocker). For example, as shown in FIG. 1, the identity of the first consumable composition and the second consumable composition may be compared to consumable composition identification data 126-3 for consumable compositions which may result in incompatible physiological responses in a user 190.

Figure 4:
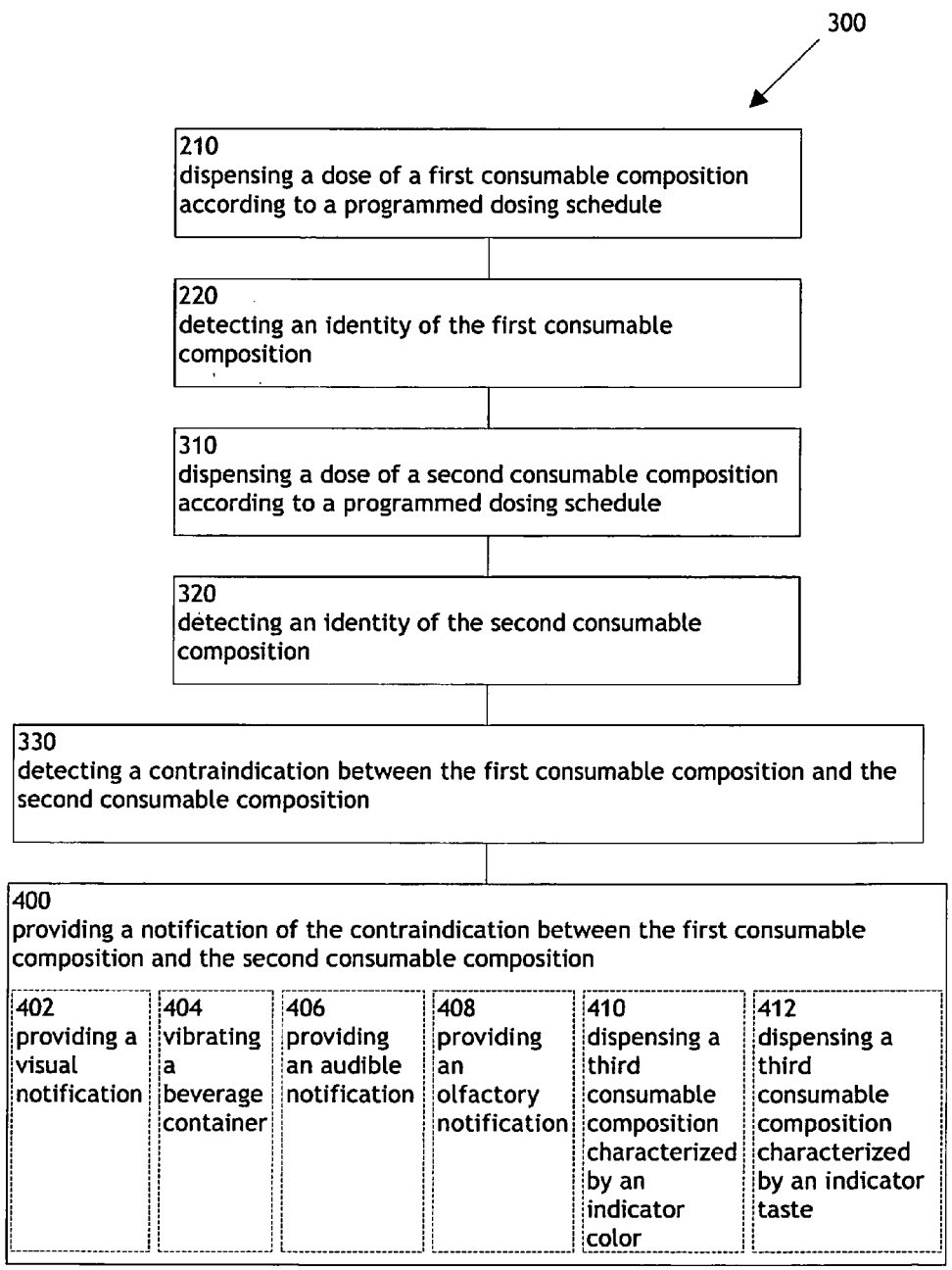
FIG. 4 is a high-level logic flowchart depicting alternate implementations of FIG. 3.

FIG. 4 illustrates alternative embodiments of the example operational flow 300 of FIG. 3. FIG. 4 illustrates example embodiments where the operation 330 may include at least one additional operation. Additional operations may include an operation 400, an operation 402, an operation 404, an operation 406, an operation 408, an operation 410 and/or an operation 412.

The operation 400 illustrates providing a notification of the contraindication between the first consumable composition and the second consumable composition (e.g. alerting a user that the ingestion of two consumable compositions will alter the medicinal or nutritional functionality of at least one of the consumable compositions). For example, as shown in FIG. 1, the user interface logic 123 may cause the notification module 142 of the user interface 140 to provide a notification to the user 190.

Further, the operation 402 illustrates providing a visual notification (e.g. an LED may change colors from green to red). For example, as shown in FIG. 1, the notification module 142 of the user interface 140 may include a flashing LED, LCD display screen, or the like.

Further, the operation 404 illustrates vibrating a beverage container (e.g. movement of an asymmetrical mass). For example, as shown in FIG. 1, the notification module 142 may include an asymmetrical rotating mass operably coupled to a motor. Upon application of power to the motor, the mass may be rotated such that it induces vibration in the beverage container 110.

The operation 406 illustrates providing an audible notification (e.g. a simple beep or voice command). For example, as shown in FIG. 1, the notification module 142 of the user interface 140 may include a speaker assembly, or the like.

The operation 408 illustrates providing an olfactory notification (e.g. an aerosol dispensation of an aromatic compound). For example, as shown in FIG. 1, the notification module 142 of the user interface 140 may include an aerosol dispensing mechanism for dispensing an odorant (e.g. dispensing into a consumable composition contained in beverage container 110 or dispensing into the atmosphere adjacent to the beverage container 110).

Further, the operation 410 illustrates dispensing a third consumable composition characterized by an indicator color (e.g. red, blue or green). For example, as shown in FIG. 1, the dispensing logic 125 may cause the integrated consumable composition dispenser module 160 and/or the external consumable composition dispenser module 170 to dispense a third consumable composition (e.g., Allura Red AC food coloring [2-naphthalenesulfonic acid]) which has a visible indicator color (e.g., red) different from the consumable composition (e.g., a white analgesic, such as acetylsalicylic acid).

Further, the operation 412 illustrates dispensing a third consumable composition characterized by an indicator taste (e.g. distinctive, foul, sour, or bitter). For example, as shown in FIG. 1, the dispensing logic 125 may cause the integrated consumable composition dispenser module 160 and/or the external consumable composition dispenser module 170 to dispense a third consumable composition (e.g., denatonium) which has an indicator taste (e.g., bitter) different from the consumable composition. The indicator taste (e.g., bitter) may be used to provide a prompt aversive reaction by the user 190, inducing the consumer to stop ingesting the consumable composition. Alternatively the indicator taste (e.g., sweet, sour) may be used as a distinctive indicator, using a taste distinctive from the normal taste of the first or second consumable compositions in order to inform the user 190 of the contraindication.

Figure 5:
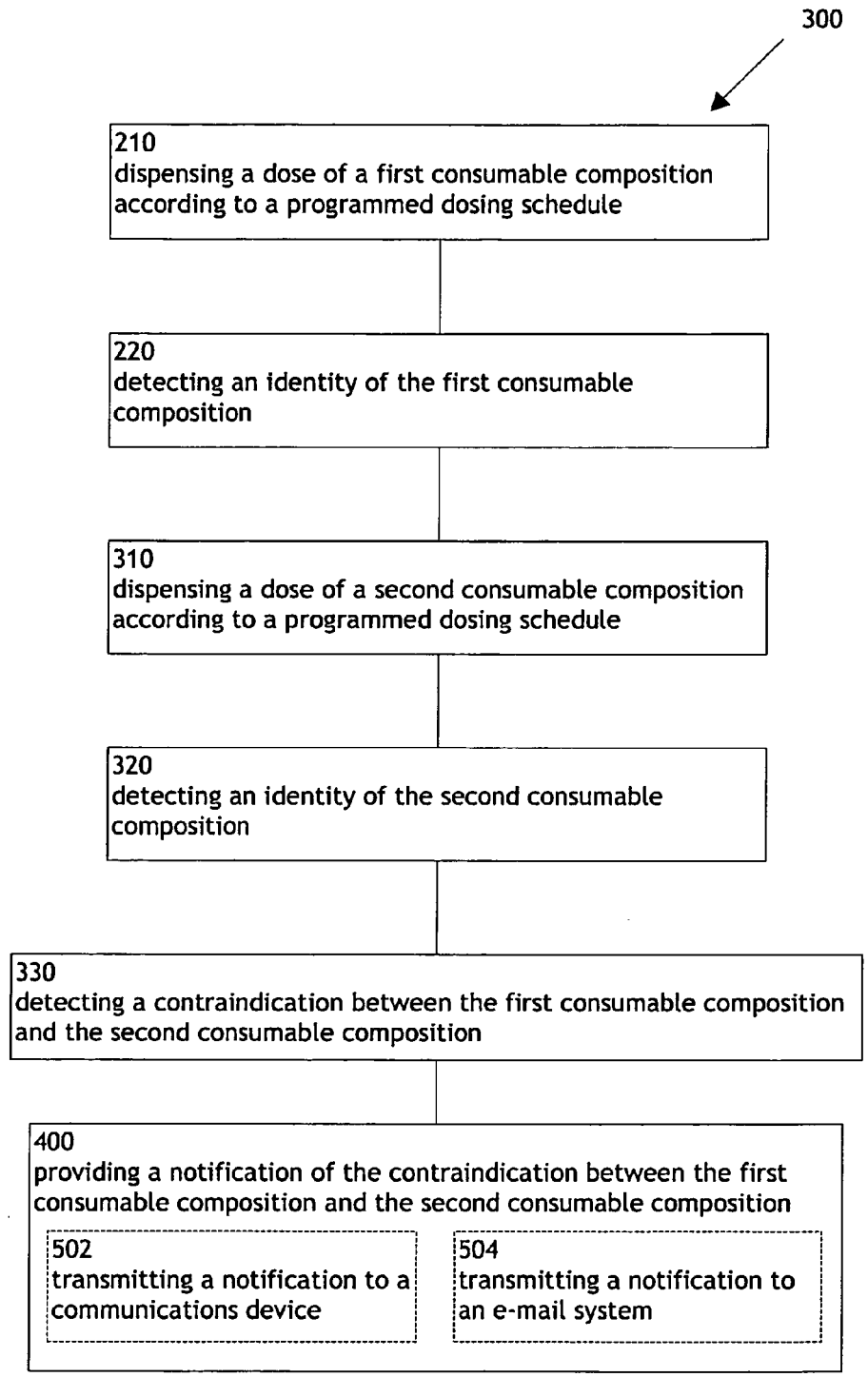
FIG. 5 is a high-level logic flowchart depicting alternate implementations of FIG. 3.

FIG. 5 illustrates alternative embodiments of the example operational flow 300 of FIG. 4. FIG. 5 illustrates example embodiments where the operation 400 may include at least one additional operation. Additional operations may include an operation 502, and/or an operation 504.

The operation 502 illustrates transmitting a notification to a communications device (e.g., placing an automated call to a user's cell phone). For example, as shown in FIG. 1, the communications module 130 may transmit a notification to a monitoring system 180 linked to a communications device 181. The communications device 181 may include a cell phone, Blackberry®, land-line phone, or the like.

Further, the operation 504 illustrates transmitting a notification to an e-mail system (e.g. sending an e-mail to an IMAP, POP3, SMTP, and/or HTTP e-mail server having an e-mail account associated with a user 190). For example, as shown in FIG. 1, the communications module 130 may transmit a notification to a monitoring system 180 linked to an e-mail system 182.

Figure 6:
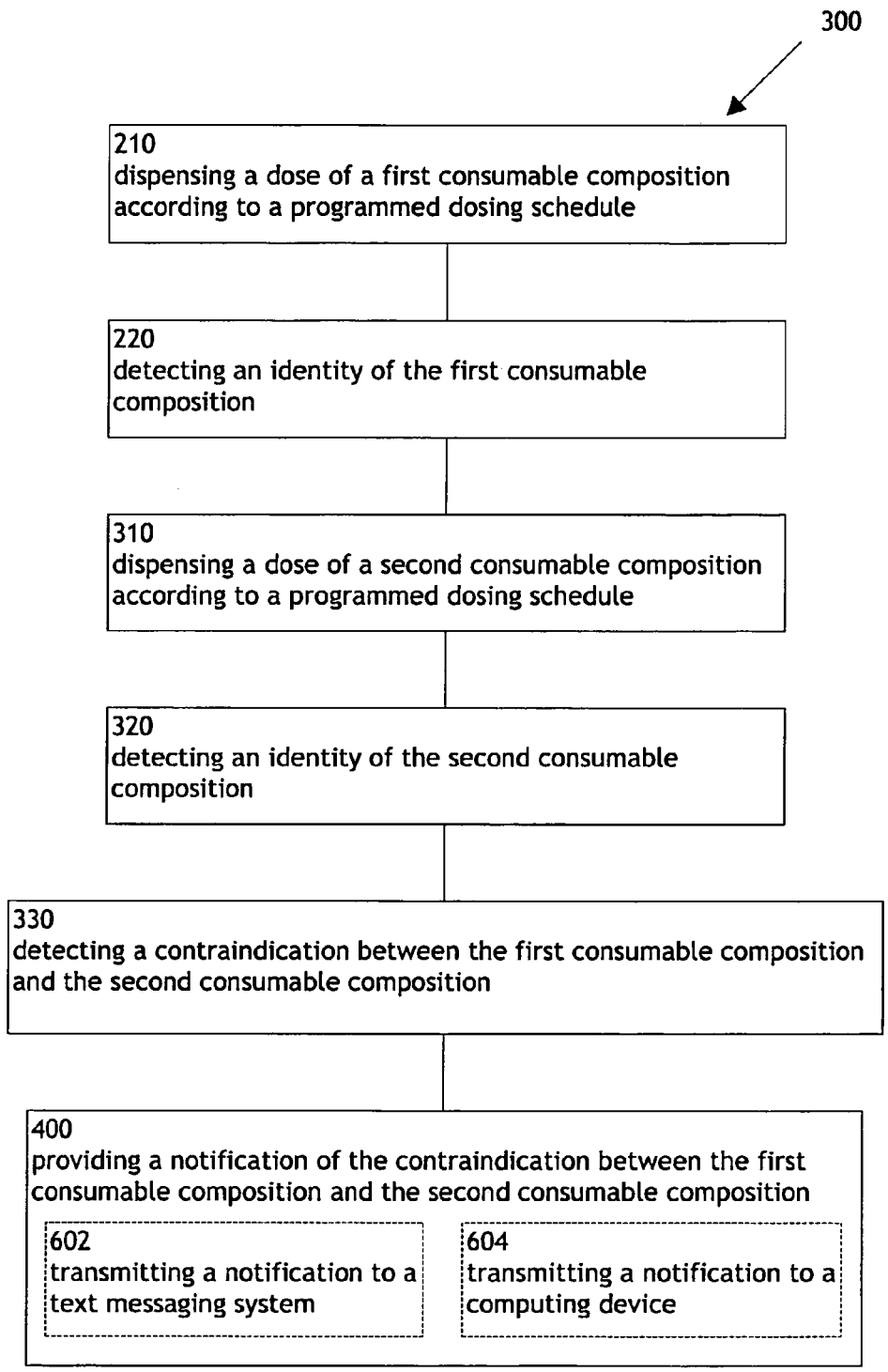
FIG. 6 is a high-level logic flowchart depicting alternate implementations of FIG. 3.

FIG. 6 illustrates alternative embodiments of the example operational flow 300 of FIG. 4. FIG. 6 illustrates example embodiments where the operation 400 may include at least one additional operation. Additional operations may include an operation 602, and/or an operation 604.

The operation 602 illustrates transmitting a notification to a text messaging system (e.g. sending text message to an SMS system in GSM). For example, as shown in FIG. 1, the communications module 130 may transmit a notification to a monitoring system 180 linked to a text messaging system 183.

Further, the operation 604 illustrates transmitting a notification to a computing device (e.g. sending an instant message to a personal computer). For example, as shown in FIG. 1, the communications module 130 may transmit a notification to a monitoring system 180 linked to a computing device 184. The computing device 184 may include a personal digital assistant (PDA), personal computer, laptop, music player, gaming device, or the like.

Figure 7:
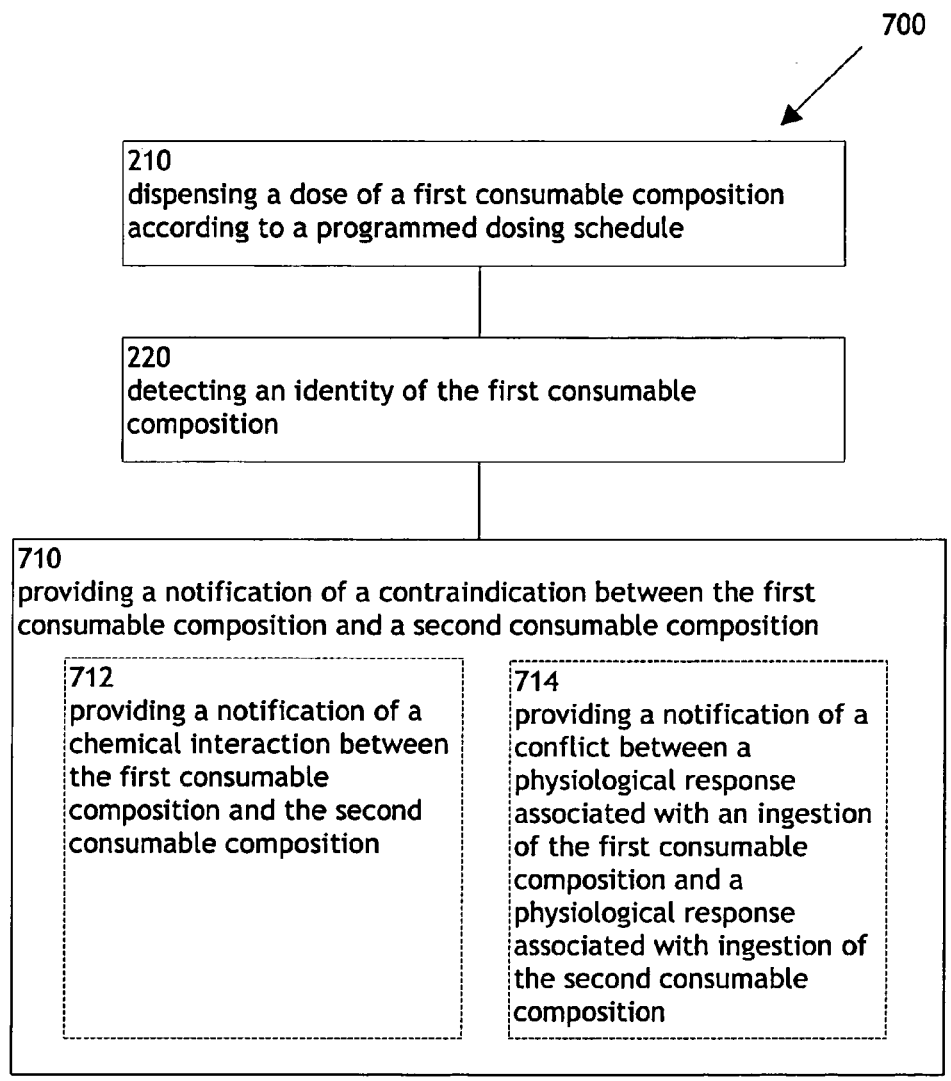
FIG. 7 is a high-level logic flowchart of a process.

FIG. 7 illustrates an operational flow 700 representing example operations related to prospective detection of interactions between dispensed consumable compositions. FIG. 7 illustrates an example embodiment where the example operational flow 200 of FIG. 2 may include at least one additional operation. Additional operations may include an operation 710, and/or operation 712.

The operation 710 illustrates providing a notification of a contraindication between the first consumable composition and a second consumable composition (e.g. providing a user with a prospective notification that a second consumable composition may have an adverse effect with a first consumable composition previously dispensed or to be dispensed). For example, as shown in FIG. 1, the identity of the first consumable composition may be compared to consumable composition identification data 126-3 for consumable compositions which may be generally contraindicated for the first consumable composition or specifically contraindicated for a particular user 190.

The operation 712 illustrates providing a notification of a chemical interaction between the first consumable composition and the second consumable composition (e.g. displaying a list of consumable compositions which may chemically react with a consumable composition to modify or nullify its functionality and should not be taken within a given time period following the ingestion of the first consumable composition). For example, as shown in FIG. 1, the identity of the first consumable composition may be compared to consumable composition identification data 126-3 for consumable compositions which will react chemically with the first consumable composition.

The operation 714 illustrates providing a notification of a conflict between a physiological response associated with an ingestion of the first consumable composition and a physiological response associated with an ingestion of the second consumable composition (e.g. displaying a list of constipatory agents which should not be taken in temporal proximity to a laxative agent). For example, as shown in FIG. 1, the identity of the first consumable composition may be compared to consumable composition identification data 126-3 for consumable compositions which will have a modifying affect on the physiological response of the first consumable composition.

Figure 8:
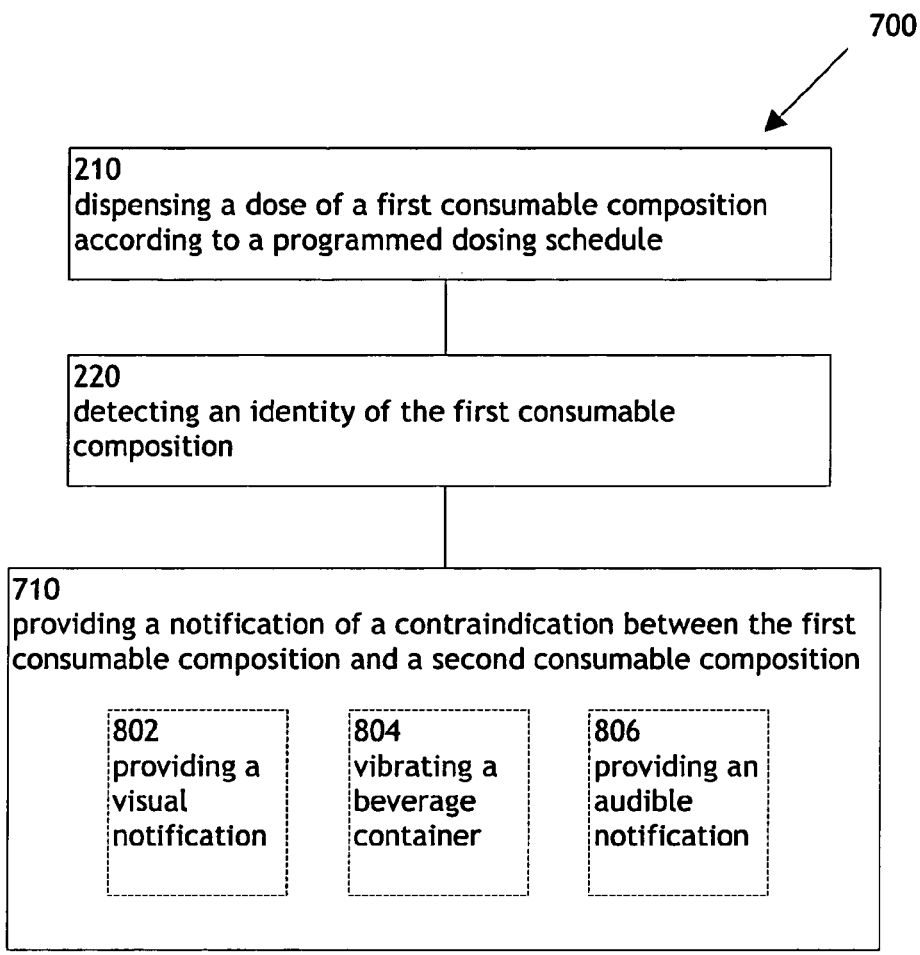
FIG. 8 is a high-level logic flowchart depicting alternate implementations of FIG. 7.

FIG. 8 illustrates alternative embodiments of the example operational flow 700 of FIG. 7. FIG. 8 illustrates an example embodiment where the example operation 710 may include at least one additional operation. Additional operations may include an operation 802, an operation 804 and/or operation 806.

The operation 802 illustrates providing a visual notification (e.g. a graphical notice on a display screen listing consumable compositions which are chemically incompatible with a consumable composition which has been dispensed or is to be dispensed). For example, as shown in FIG. 1, the notification module 142 of the user interface 140 may include a LCD display screen, an LCoS display screen, or the like.

The operation 804 illustrates vibrating a beverage container (e.g. movement of an asymmetrical mass when programmed dosing schedules for incompatible consumable compositions overlap). For example, as shown in FIG. 1, the notification module 142 may include an asymmetrical rotating mass operably coupled to a motor. Upon detection of an overlap in dispensing programs 126-2 for incompatible consumable compositions, power may be applied to the motor and the mass may be rotated such that it induces vibration in the beverage container 110.

The operation 806 illustrates providing an audible notification (e.g. a voice reciting a list of consumable compositions which are chemically incompatible with a consumable composition which has been dispensed or is to be dispensed). For example, as shown in FIG. 1, the notification module 142 of the user interface 140 may include a speaker assembly, or the like.

Figure 9:
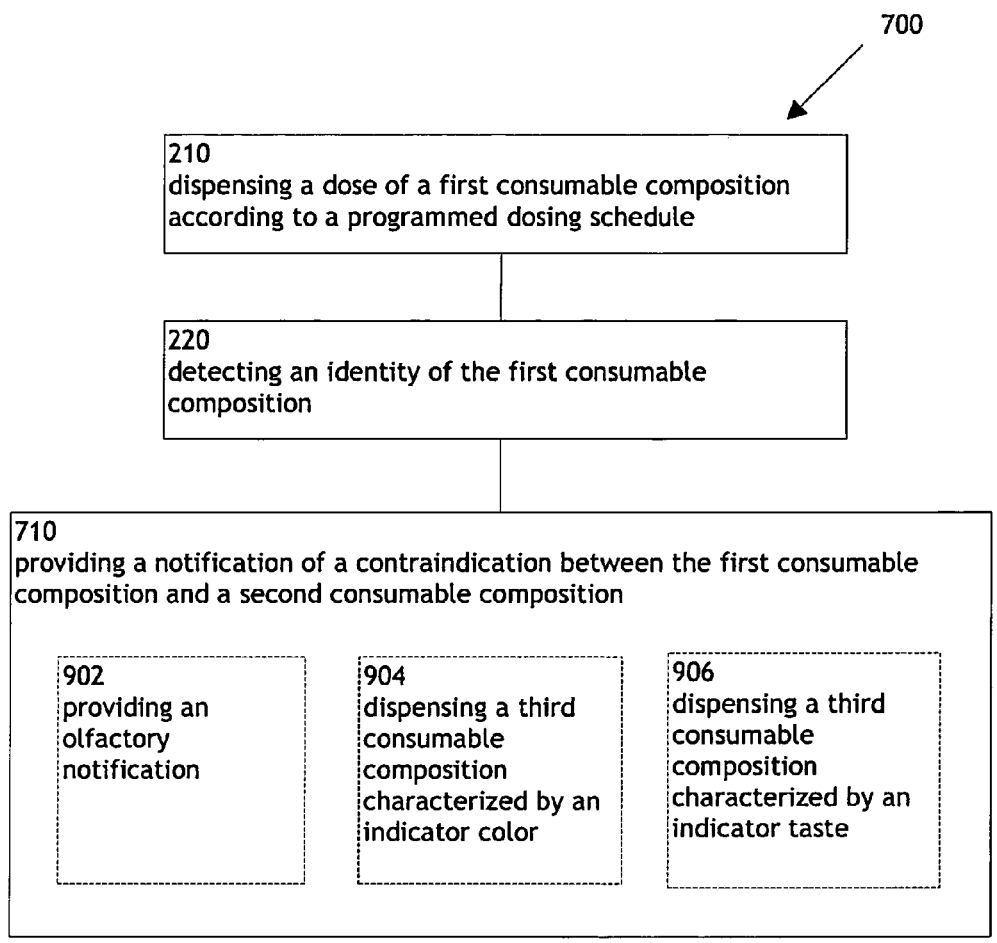
FIG. 9 is a high-level logic flowchart depicting alternate implementations of FIG. 7.

FIG. 9 illustrates alternative embodiments of the example operational flow 700 of FIG. 7. FIG. 9 illustrates an example embodiment where the example operation 710 may include at least one additional operation. Additional operations may include an operation 902, an operation 904, and/or an operation 906.

The operation 902 illustrates providing an olfactory notification (e.g. an aerosol dispensation of an aromatic compound). For example, as shown in FIG. 1, the notification module 142 of the user interface 140 may include an aerosol dispensing mechanism for dispensing an odorant (e.g. dispensing into a consumable composition contained in beverage container 110 or dispensing into the atmosphere adjacent to the beverage container 110).

The operation 904 illustrates dispensing a third consumable composition characterized by an indicator color (e.g. red, blue or green). For example, as shown in FIG. 1, the dispensing logic 125 may cause the integrated consumable composition dispenser module 160 and/or the external consumable composition dispenser module 170 to dispense a third consumable composition (e.g., Sunset Yellow FCF food coloring [disodium salt of 6-hydroxy-5-[(4-sulfophenyl)azo]-2-naphthalenesulfonic acid]) separate from the consumable composition which has a visible indicator color (e.g. yellow) different than the color of the consumable composition (e.g. a white antihistamine).

Further, the operation 906 illustrates dispensing a third consumable composition characterized by an indicator taste (e.g. distinctive, foul, sour, or bitter). For example, as shown in FIG. 1, the dispensing logic 125 may cause the integrated consumable composition dispenser module 160 and/or the external consumable composition dispenser module 170 to dispense a third consumable composition (e.g., denatonium) which has an indicator taste (e.g., bitter) different from the consumable composition. The indicator taste (e.g., bitter) may be used to provide a prompt aversive reaction by the user 190, inducing the consumer to stop ingesting the consumable composition. Alternatively the indicator taste (e.g., sweet, sour) may be used as a distinctive indicator, using a taste distinctive from the normal taste of the first or second consumable compositions in order to inform the user 190 of the contraindication.

Figure 10:
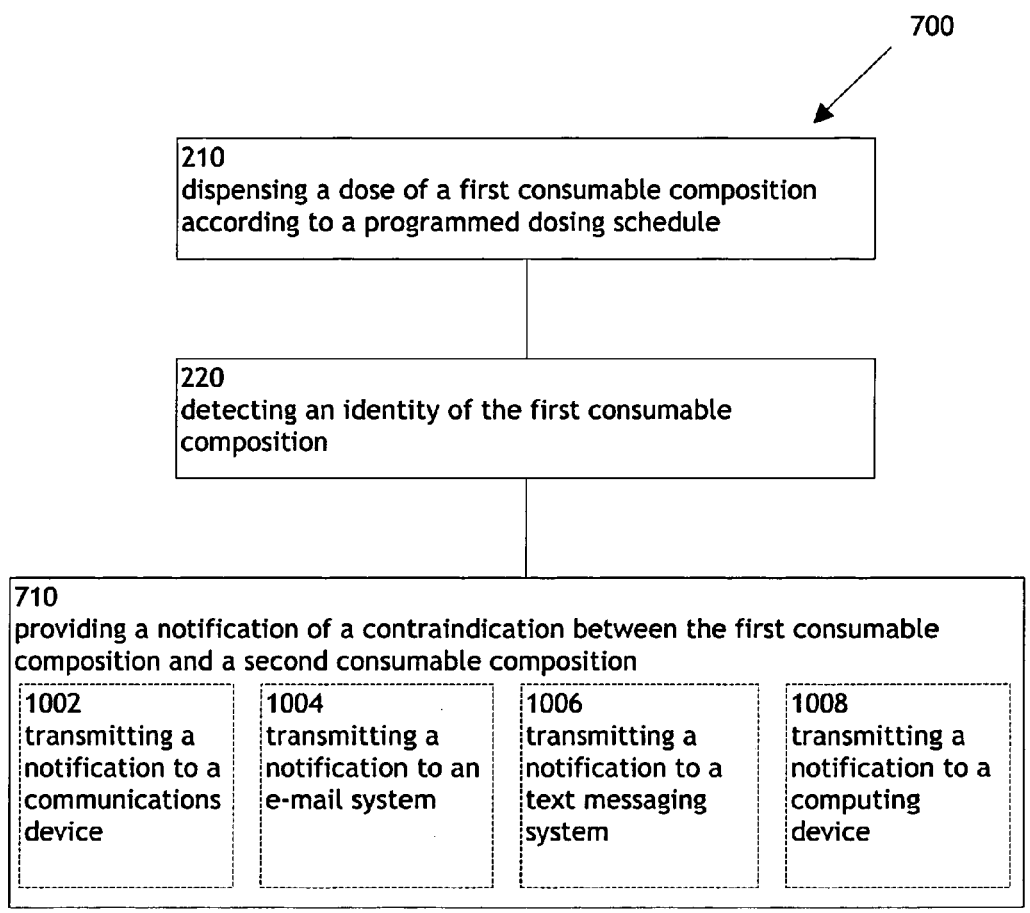
FIG. 10 is a high-level logic flowchart depicting alternate implementations of FIG. 7.

FIG. 10 illustrates alternative embodiments of the example operational flow 700 of FIG. 7. FIG. 10 illustrates example embodiments where the operation 710 may include at least one additional operation. Additional operations may include an operation 1002, an operation 1004, an operation 1006, and/or an operation 1008.

The operation 1002 illustrates transmitting a notification to a communications device (e.g. sending an instant message to a Blackberry® device). For example, as shown in FIG. 1, the communications module 130 may transmit a notification to a monitoring system 180 linked to a communications device 181. The communications device 181 may include a cell phone, Blackberry®, land-line phone, or the like.

The operation 1004 illustrates transmitting a notification to an e-mail system (e.g. an e-mail to an IMAP, POP3, SMTP, and/or HTTP e-mail server having an e-mail account associated with a user 190). For example, as shown in FIG. 1, the communications module 130 may transmit a notification to a monitoring system 180 linked to an e-mail system 182.

The operation 1006 illustrates transmitting a notification to a text messaging system (e.g. text message to an SMS system in GSM). For example, as shown in FIG. 1, the communications module 130 may transmit a notification to a monitoring system 180 linked to a text messaging system 183.

The operation 1008 illustrates transmitting a notification to a computing device (e.g., an instant message to a PDA). For example, as shown in FIG. 1, the communications module 130 may transmit a notification to a monitoring system 180 linked to a computing device 184. The computing device 184 may include a personal digital assistant (PDA), personal computer, laptop, music player, gaming device, or the like.

Figure 11:
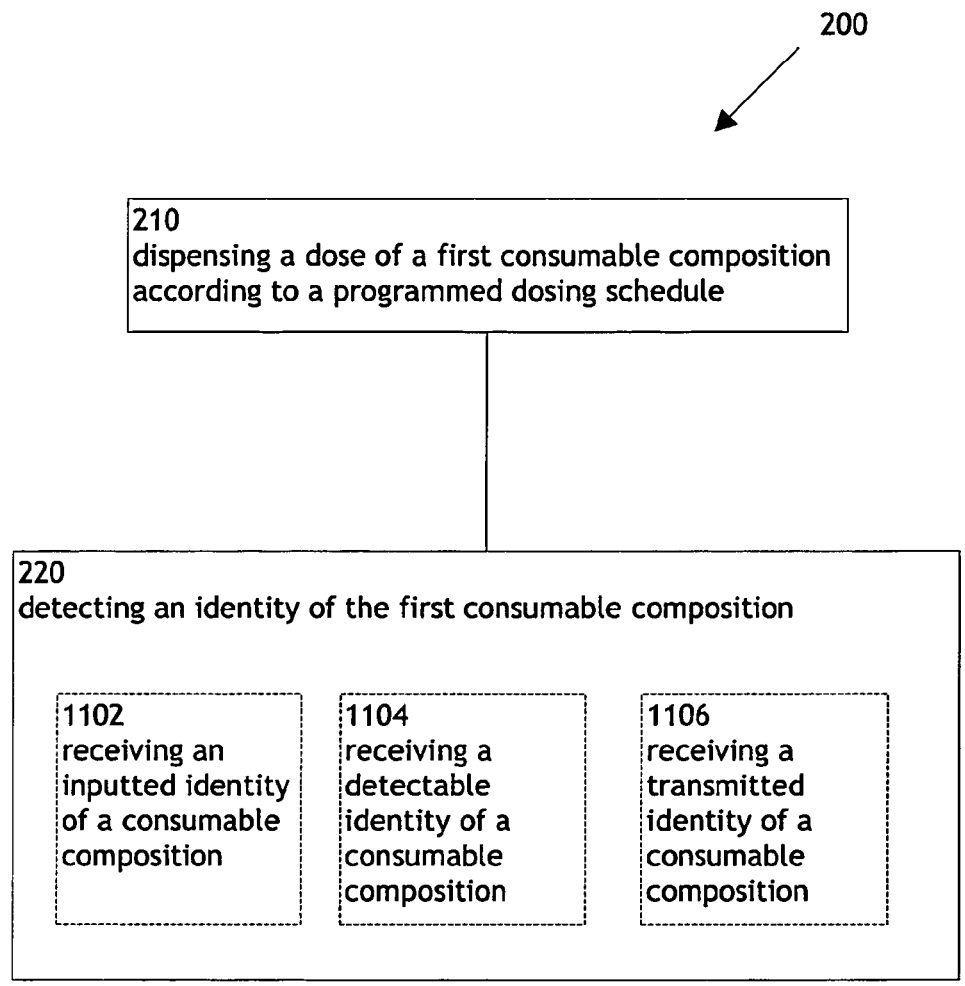
FIG. 11 is a high-level logic flowchart depicting alternate implementations of FIG. 2.

FIG. 11 illustrates alternative embodiments of the example operational flow 200 of FIG. 2. FIG. 11 illustrates example embodiments where the operation 220 may include at least one additional operation. Additional operations may include an operation 1102, an operation 1104 and/or an operation 1106.

The operation 1102 illustrates receiving an inputted identity of a consumable composition (e.g. receipt of a user input identifying a consumable composition whose functionality may be affected by a second consumable composition). For example, as shown in FIG. 1, a user 190 may input an identity of a consumable composition via an input module 146 (e.g. a touch screen) of a user interface 140.

The operation 1104 illustrates receiving a detectable identity of a consumable composition (e.g. receipt of identification data from a label identifying a consumable composition whose functionality may be affected by a second consumable composition). For example, as shown in FIG. 1, the input module 146 of user interface 140 may include a bar code reader for reading a barcode from a label on a container for a consumable composition.

The operation 1106 illustrates receiving a transmitted identity of a consumable composition (e.g. receipt of identification data from a physician identifying a consumable composition whose functionality may be affected by a second consumable composition). For example, as shown in FIG. 1, the communications module 130, may receive consumable composition identification data from a monitoring system 180 (e.g. a system associated with a physician, a system associated with a consumable composition supply entity, or the like).

Those having skill in the art will recognize that the state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In some implementations described herein, logic and similar implementations may include software or other control structures suitable to operation. Electronic circuitry, for example, may manifest one or more paths of electrical current constructed and arranged to implement various logic functions as described herein. In some implementations, one or more media are configured to bear a device-detectable implementation if such media hold or transmit a special-purpose device instruction set operable to perform as described herein. In some variants, for example, this may manifest as an update or other modification of existing software or firmware, or of gate arrays or other programmable hardware, such as by performing a reception of or a transmission of one or more instructions in relation to one or more operations described herein. Alternatively or additionally, in some variants, an implementation may include special-purpose hardware, software, firmware components, and/or general-purpose components executing or otherwise invoking special-purpose components. Specifications or other implementations may be transmitted by one or more instances of tangible transmission media as described herein, optionally by packet transmission or otherwise by passing through distributed media at various times.

Alternatively or additionally, implementations may include executing a special-purpose instruction sequence or otherwise invoking circuitry for enabling, triggering, coordinating, requesting, or otherwise causing one or more occurrences of any functional operations described above. In some variants, operational or other logical descriptions herein may be expressed directly as source code and compiled or otherwise invoked as an executable instruction sequence. In some contexts, for example, C++ or other code sequences can be compiled directly or otherwise implemented in high-level descriptor languages (e.g., a logic-synthesizable language, a hardware description language, a hardware design simulation, and/or other such similar mode(s) of expression). Alternatively or additionally, some or all of the logical expression may be manifested as a Verilog-type hardware description or other circuitry model before physical implementation in hardware, especially for basic operations or timing-critical applications. Those skilled in the art will recognize how to obtain, configure, and optimize suitable transmission or computational elements, material supplies, actuators, or other common structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, those skilled in the art will recognize that the various aspects described herein which can be implemented, individually and/or collectively, by a wide range of hardware, software, firmware, and/or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). Those having skill in the art will recognize that the subject matter described herein may be implemented in an analog or digital fashion or some combination thereof.

Those skilled in the art will recognize that at least a portion of the devices and/or processes described herein can be integrated into a data processing system. Those having skill in the art will recognize that a data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system may be implemented utilizing suitable commercially available components, such as those typically found in data computing/communication and/or network computing/communication systems.

Those skilled in the art will recognize that it is common within the art to implement devices and/or processes and/or systems, and thereafter use engineering and/or other practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Qwest, Southwestern Bell, etc.), or (g) a wired/wireless services entity (e.g., Sprint, Cingular, Nextel, etc.), etc.

In certain cases, use of a system or method may occur in a territory even if components are located outside the territory. For example, in a distributed computing context, use of a distributed computing system may occur in a territory even though parts of the system may be located outside of the territory (e.g., relay, server, processor, signal-bearing medium, transmitting computer, receiving computer, etc. located outside the territory).

A sale of a system or method may likewise occur in a territory even if components of the system or method are located and/or used outside the territory.

Further, implementation of at least part of a system for performing a method in one territory does not preclude use of the system in another territory.

Although user 190 is shown/described herein as a single illustrated figure, those skilled in the art will appreciate that user 190 may be representative of a human user, a robotic user (e.g., computational entity), and/or substantially any combination thereof (e.g., a user may be assisted by one or more robotic agents) unless context dictates otherwise. Those skilled in the art will appreciate that, in general, the same may be said of "sender" and/or other entity-oriented terms as such terms are used herein unless context dictates otherwise.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

In some instances, one or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms. For example, the phrase "A or B" will be typically understood to include the possibilities of "A" or "B" or "A and B."

With respect to the appended claims, those skilled in the art will appreciate that recited operations therein may generally be performed in any order. Also, although various operational flows are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to" or other past-tense adjectives are generally not intended to exclude such variants, unless context dictates otherwise.

What is claimed is:

1. A method for administering a consumable composition, the method comprising:
    controlling dispensing a dose of a first consumable composition according to a programmed dosing schedule;
    determining an identity of the first consumable composition from chemical composition identity data obtained via at least one receiver;
    obtaining an identity of at least one second consumable composition;
    determining a chemical incompatibility of the first consumable composition and the at least one second consumable composition by comparing at least an identity of the first consumable composition determined from chemical composition identity data and an identity of the at least one second composition to chemically incompatible composition data; and
    generating electronic user notification data indicating the chemical incompatibility of the first consumable composition and the at least one second consumable composition.

2. A system comprising:
    at least one computing device programmed for:
        controlling dispensing a dose of a first consumable composition according to a programmed dosing schedule;
        determining an identity of the first consumable composition from chemical composition identity data obtained via at least one receiver;
        obtaining an identity of at least one second consumable composition;
        determining a chemical incompatibility of the first consumable composition and the at least one second consumable composition by comparing at least an identity of the first consumable composition determined from chemical composition identity data and an identity of the at least one second composition to chemically incompatible composition data; and
        generating electronic user notification data indicating the chemical incompatibility of the first consumable composition and the at least one second consumable composition.

3. The system of claim 2, wherein the generating electronic user notification data indicating the chemical incompatibility of the first consumable composition and the at least one second consumable composition includes:
    generating electronic visual notification data indicating the chemical incompatibility of the first consumable composition and the at least one second consumable composition.

4. The system of claim 2, wherein the generating electronic user notification data indicating the chemical incompatibility of the first consumable composition and the at least one second consumable composition includes:
    generating electronic container vibration data configured to cause vibration of a container configured to receive a dispensed dose of at least one of the first consumable composition or the at least one second consumable composition.

5. The system of claim 2, wherein the generating electronic user notification data indicating the chemical incompatibility of the first consumable composition and the at least one second consumable composition includes:

generating electronic audible notification data indicating the chemical incompatibility of the first consumable composition and the at least one second consumable composition.

6. The system of claim 2, wherein the generating electronic user notification data indicating the chemical incompatibility of the first consumable composition and the at least one second consumable composition includes:
dispensing a third consumable composition characterized by an indicator color indicating the chemical incompatibility of the first consumable composition and the at least one second consumable composition.

7. The system of claim 2, wherein the generating electronic user notification data indicating the chemical incompatibility of the first consumable composition and the at least one second consumable composition includes:
transmitting electronic notification data indicating the chemical incompatibility of the first consumable composition and the at least one second consumable composition to a communications device.

8. The system of claim 2, wherein the generating electronic user notification data indicating the chemical incompatibility of the first consumable composition and the at least one second consumable composition further comprises:
transmitting electronic notification data indicating the chemical incompatibility of the first consumable composition and the at least one second consumable composition to an e-mail system.

9. The system of claim 2, wherein the generating electronic user notification data indicating the chemical incompatibility of the first consumable composition and the at least one second consumable composition includes:
transmitting electronic notification data indicating the chemical incompatibility of the first consumable composition and the at least one second consumable composition to a text messaging system.

10. The system of claim 2, wherein the generating electronic user notification data indicating the chemical incompatibility of the first consumable composition and the at least one second consumable composition includes:
transmitting electronic notification data indicating the chemical incompatibility of the first consumable composition and the at least one second composition to a computing device.

11. The system of claim 2, wherein the obtaining an identity of at least one second composition includes:
receiving a user-inputted identity of the at least one second composition.

12. The system of claim 2, wherein the obtaining an identity of at least one second composition includes:
receiving a transmitted identity of the at least one second composition.

13. The system of claim 2, wherein the composition identity data includes at least one of:
photoionization sensor data, spectroscopic sensor data, spectrometric sensor data, crystallographic sensor data, electrochemical sensor data, or calorimetric sensor data.

14. The system of claim 2, wherein the composition identity data includes chemical composition sensor data obtained from at least one sensor operably coupled to at least one container configured to receive a dispensed dose of the first consumable composition.

15. The system of claim 2, wherein the incompatible composition data includes:
data indicative of two or more compositions, wherein at least a first composition of the two or more compositions alters at least one of the medicinal or nutritional functionality of at least a second composition of the two or more compositions.

16. The system of claim 2, wherein the composition identity data includes at least one of:
photoionization sensor data, spectroscopic sensor data, spectrometric sensor data, crystallographic sensor data, electrochemical sensor data, or calorimetric sensor data.

17. The system of claim 2, wherein the determining an identity of the first consumable composition from composition identity data obtained via at least one receiver includes:
determining an identity of the first consumable composition from composition identity data obtained via at least one user input device.

18. The system of claim 2, wherein the determining an identity of the first consumable composition from composition identity data obtained via at least one receiver includes:
determining an identity of the first consumable composition from composition identity data obtained via at least one sensor.

19. The system of claim 2, wherein the determining an identity of the first consumable composition from composition identity data obtained via at least one sensor includes:
determining an identity of the first consumable composition from composition identity data obtained via at least one optical sensor.

20. At least one computing device comprising:
electronic circuitry configured for:
controlling dispensing a dose of a first consumable composition according to a programmed dosing schedule;
determining an identity of the first consumable composition from chemical-composition identity data obtained via at least one receiver;
obtaining an identity of at least one second consumable composition;
determining a chemical incompatibility of the first consumable composition and the at least one second consumable composition by comparing at least an identity of the first consumable composition determined from chemical composition identity data and an identity of the at least one second composition to chemically incompatible composition data; and
generating electronic user notification data indicating the chemical incompatibility of the first consumable composition and the at least one second consumable composition.

* * * * *